Sept. 5, 1944. S. B. ROBERTS Plant Pat. 641
ROSE PLANT
Filed April 14, 1944
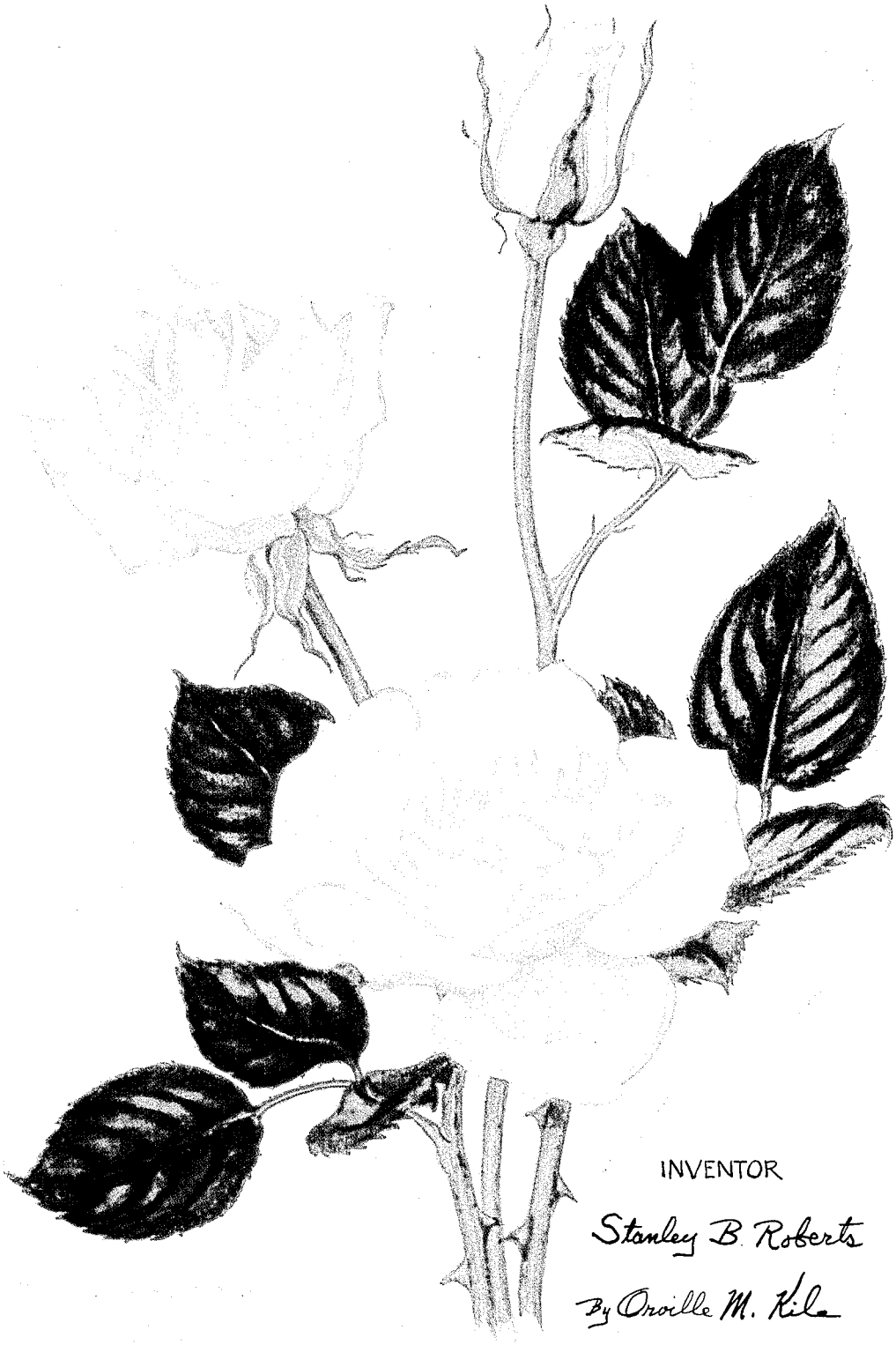
INVENTOR
Stanley B. Roberts
By Oroille M. Kile
PLANT PATENT AGENT Patented Sept. 5, 1944

Plant Pat. 641

UNITED STATES PATENT OFFICE

641

ROSE PLANT

Stanley B. Roberts, Madison, N. J.

Application April 14, 1944, Serial No. 531,005

1 Claim. (Cl. 47—61)

My present invention relates to a new and distinct variety of hybrid tea rose plant and was produced by me as a result of definite breeding efforts. The new variety is of the greenhouse forcing type. Its parents are Better Times and Orange of Nassau, which were crossed by me at my greenhouses in Madison, New Jersey.

The original illustrations which are a part of this specification show in full color three specimens of the blossoms of this new variety in various stages of opening and in approximately their true colors.

Following is a detailed description of the plant and flower of this new variety of rose plant. Color references indicate Ridgway's Color Standards and Nomenclature.

*The plant*

Growth habit: Vigorous bush. Much like the growth of the variety Rapture.

Blooming habit: Perpetual and free-blooming.

Foliage: Abundant. Leaves compound, with 3 to 7 leaflets.

*Leaflets.*—Size—Large terminal leaflet approximately 3½ inches by 2½ inches. Shape—Oval with acute apex. Color—Very dark green with veins and edge usually dark red. Texture—Leathery. Edge—Sharply serrated; usually approximately Brick Red (Plate XIII).

*Stipules.*—Narrow; medium length; clinging for most of their length.

*Rachis.*—Heavy; red; grooved above, with small thorns on under side.

*Stems.*—Strong and upright. Color considerably lighter than foliage (approximately Oil Green, Plate V). Many large red thorns are found on the stems, and small spines are found on the peduncle.

*Disease resistance.*—Excellent.

*The flower*

Bud:

*Form.*—Long and pointed, rather wide at base. As it begins to open it becomes somewhat urn-shaped.

*Size.*—1½ inches to 2 inches long.

*Color.*—Coppery pink, between Geranium Pink and Peach Red (Plate I), with a large aiglet of Apricot Yellow (Plate IV).

*Peduncle.*—Relatively short; sturdy; approximately same color as stems.

Bloom:

*Size.*—Large, measuring 4 to 5 inches in diameter.

*Form.*—Loosely, deeply cupped, later opening flatter. Appears full and large although there are few petals.

*Petalage.*—Double, averaging about 22 petals.

*Color.*—Flower beginning to open is, on the outer surface of petals, between Peach Red (Plate I) and Light Jasper Red (Plate XIII), blending into a yellow base. At this stage the inner surface of petals is between Alizarine Pink (Plate XIII) and Spinel Pink (Plate XXVI). As the flower opens wider, more of the inner surface of the petals is visible and the entire flower therefore has more of the pink appearance, with a greater amount of the yellow aiglet in evidence. After the flower has been fully open for a day or two and only the inner surface of the petals is visible, the tone has become much more delicate, the entire flower appearing to be Jasper Pink (Plate XIII) to Thulite Pink (Plate XXVI), blending into a large yellow aiglet.

*Petals.*—Outer petals are large and deeply cupped. They measure 2 to 2⅛ inches wide by 2¼ to 2½ inches long.

*Fragrance.*—Delicate and pleasing.

*Keeping quality.*—Excellent both on the plant and after being cut.

*Sepals.*—Long and slender; only slightly foliaceous; outer surface approximately the same color as stems.

*Stamens.*—Anthers and filaments are approximately the same color (Light Cadmium, Plate IV), although the filaments are tinged with red which increases in intensity toward their base.

*Pistils.*—Slightly lighter yellow than the stamens. Shorter than stamens.

Having thus disclosed my invention, I claim:

The new and distinct variety of hybrid tea rose plant, substantially as herein shown and described, characterized particularly by its vigorous growth; its red-veined and red-edged large dark foliage; its coppery pink buds; and its bloom of distinctive coppery pink color as indicated.

STANLEY B. ROBERTS.